US011266795B2

(12) United States Patent
Vasandani et al.

(10) Patent No.: US 11,266,795 B2
(45) Date of Patent: *Mar. 8, 2022

(54) BREATH ACTUATED NEBULIZER

(71) Applicant: INSPIRX, INC., Durham, NC (US)

(72) Inventors: Paresh Vasandani, Somerset, NJ (US); Vijay Shukla, Highland Park, NJ (US); K. Mosaddeq Hossain, Hillborough, NJ (US); Rohinton D. Toddywala, Somerset, NJ (US)

(73) Assignee: INSPIRX, INC., Durham, NC (US)

( * ) Notice: Subject to any disclaimer, the term of this patent is extended or adjusted under 35 U.S.C. 154(b) by 124 days.

This patent is subject to a terminal disclaimer.

(21) Appl. No.: 16/674,184

(22) Filed: Nov. 5, 2019

(65) Prior Publication Data
US 2020/0069893 A1 Mar. 5, 2020

Related U.S. Application Data

(63) Continuation of application No. 15/023,488, filed as application No. PCT/US2014/056448 on Sep. 19, 2014, now Pat. No. 10,463,813.
(Continued)

(51) Int. Cl.
*A61M 11/06* (2006.01)
*A61M 15/00* (2006.01)
(Continued)

(52) U.S. Cl.
CPC ........ *A61M 11/06* (2013.01); *A61M 15/0015* (2014.02); *A61M 15/0018* (2014.02);
(Continued)

(58) Field of Classification Search
CPC .......... A61M 5/14586; A61M 5/14593; A61M 11/002; A61M 11/003; A61M 11/00;
(Continued)

(56) References Cited

U.S. PATENT DOCUMENTS 4,588,129 A 5/1986 Shanks
5,020,527 A 6/1991 Dessertine
(Continued)

FOREIGN PATENT DOCUMENTS

EP 0532349 A2 3/1993
EP 1 402 912 A2 3/2004
(Continued)

OTHER PUBLICATIONS

Notification of Reason(s) for Refusal issued in corresponding Japanese Patent Application No. 2016-544005 dated Aug. 7, 2018.
(Continued)

*Primary Examiner* — Tu A Vo
*Assistant Examiner* — Alexander Morales
(74) *Attorney, Agent, or Firm* — Jonathan D. Ball; Greenberg Traurig, LLP (57) ABSTRACT

A breath actuated nebulizer for administration of an inhaled medication to a patient is provided with a generally cylindrical body in a horizontal orientation to the patient. Within the body is a Venturi configured to nebulizer a liquid medication in a reservoir. Within the body is a shaft integrated with a baffle and diaphragm that slides horizontally in response to the breathing of a patient. During inhalation by the patient, the diaphragm flexes shifting the baffle over the Venturi, allowing nebulization to occur. When the patient exhales, the diaphragm flexes to a default position in which the baffle is distal to the Venturi, thereby stopping the nebulization. The diaphragm is biased to rest in this default position until the patient inhales again.

10 Claims, 8 Drawing Sheets

Related U.S. Application Data (60) Provisional application No. 61/880,880, filed on Sep. 21, 2013.

(51) Int. Cl.
| | | |
|---|---|---|
| *A61M 16/06* | (2006.01) | |
| *A61M 16/10* | (2006.01) | |
| *A61M 16/14* | (2006.01) | |
| *A61M 11/00* | (2006.01) | |
| *A61M 16/08* | (2006.01) | |

(52) U.S. Cl.
CPC .... *A61M 15/0021* (2014.02); *A61M 15/0091* (2013.01); *A61M 16/06* (2013.01); *A61M 16/1065* (2014.02); *A61M 16/14* (2013.01); *A61M 11/002* (2014.02); *A61M 16/0825* (2014.02); *A61M 2205/581* (2013.01)

(58) Field of Classification Search
CPC ................ A61M 11/065; A61M 19/00; A61M 15/0013; A61M 15/0091; A61M 15/0095; A61M 16/20; A61M 16/201; A61M 16/206–209; A61M 39/22; A61M 39/24; A61M 2039/2486; A61M 2039/2473
USPC ............ 128/200.14–200.24, 203.12, 203.21, 128/203.23–203.25, 204.14, 204.18, 128/207.14–207.18, 203.15, 203.16, 128/204.23, 205.24; 604/58, 94.01; 239/338, 370, 428
See application file for complete search history.

(56) References Cited

U.S. PATENT DOCUMENTS

| | | | |
|---|---|---|---|
| 5,239,992 A * | 8/1993 | Bougamont | A61M 15/0065 128/203.12 |
| 5,687,912 A | 11/1997 | Denyer | |
| 5,813,401 A | 9/1998 | Radcliff et al. | |
| 5,823,179 A | 10/1998 | Grychowski et al. | |
| 5,848,587 A * | 12/1998 | King | A61M 11/002 128/200.18 |
| 5,881,722 A * | 3/1999 | DeVries | G01F 1/40 128/204.21 |
| 6,041,779 A | 3/2000 | Juusela | |
| 6,105,929 A * | 8/2000 | Davenport | A61M 16/0858 251/63.6 |
| 6,131,568 A | 10/2000 | Denyer et al. | |
| 6,186,477 B1 * | 2/2001 | McCombs | A61M 16/20 128/205.24 |
| 6,443,151 B1 * | 9/2002 | Ruskewicz | A61M 15/00 128/200.24 |
| 6,578,571 B1 | 6/2003 | Watt | |
| 6,644,304 B2 | 11/2003 | Grychowski et al. | |
| 6,732,732 B2 | 5/2004 | Edwards et al. | |
| 6,772,754 B1 * | 8/2004 | Mendenhall | A61M 15/0091 128/200.14 |
| 6,857,427 B2 | 2/2005 | Ziegler et al. | |
| RE40,591 E | 12/2008 | Denyer | |
| 7,841,335 B2 | 11/2010 | Harrington et al. | |
| 8,074,642 B2 | 12/2011 | Bruce et al. | |
| 2002/0157663 A1 | 10/2002 | Blacker et al. | |
| 2003/0015193 A1 | 1/2003 | Grychowski et al. | |
| 2007/0023036 A1 | 2/2007 | Grychowski et al. | |
| 2010/0236545 A1 | 9/2010 | Kern | |
| 2010/0258114 A1 | 10/2010 | Cortez, Jr. et al. | |
| 2011/0114090 A1 | 5/2011 | Piper | |

FOREIGN PATENT DOCUMENTS

| | | |
|---|---|---|
| JP | 11-506642 A | 6/1996 |
| JP | 2000-504603 A | 4/2000 |
| JP | 2008-161528 A | 7/2008 |
| WO | WO 97/29799 A1 | 8/1997 |
| WO | WO 2012/173992 A1 | 12/2012 |

OTHER PUBLICATIONS

International Search Report dated Dec. 25, 2014 issued in PCT/US2014/056448.

Supplementary European Search Report issued in European Application No. EP 14 84 5665 dated May 3, 2017.

\* cited by examiner

BREATH ACTUATED NEBULIZER

CROSS-REFERENCE TO RELATED APPLICATIONS

This application is a continuation application of U.S. patent application Ser. No. 15/023,488 filed Mar. 21, 2016, which claims the benefit of U.S. Provisional Application No. 61/880,880 filed on Sep. 21, 2013, the entire contents of which are incorporated herein by reference.

FIELD OF THE INVENTION

This disclosure pertains to nebulizers for the administration of inhaled aerosol drugs.

BACKGROUND

In the field of respiratory devices, nebulizers are important devices used for the inhalation of drugs in the form of an aerosol to patients in need of a drug administered directly into the lungs. A nebulizer employs an apparatus that generates an aerosol or mist from a solution (usually an aqueous solution) or suspension of a drug. The mist may be an aerosolized suspension or an atomized suspension of drug, meaning micro-droplets suspended in air, medical oxygen, or other inhalable gas. The aerosol is conveyed to the mouth and/or nose of a patient and inhaled into the lungs. In some cases, the mist is conveyed to the lungs through a mouthpiece. In other cases, the nebulizer may be coupled to an inhalation mask.

Several nebulization technologies are known, including gas-jet, ultrasonic, and vibrating mesh nebulizers. This disclosure pertains to gas-jet nebulizers, which operate using a Venturi, wherein a jet of pressurized gas (air or other suitable gas, such as medical oxygen) is directed over an orifice on a capillary that is connected to a reservoir containing a drug in aqueous solution. The Venturi creates a localized low pressure zone that draws the drug solution out of the capillary orifice and into the air jet, where the liquid is atomized by a shearing effect. Typically, a baffle is employed in the jet effluent to assist in the formation of appropriate size droplets in the nebulized stream. In addition, a baffle prevents large droplets from exiting the device, so that only aerosol micro-droplets of drug containing solution exit the device. Still further, in many nebulizer designs, a baffle may be required to deflect the low pressure zone created by a Venturi jot over a liquid orifice in communication with the drug reservoir. In such designs, the baffle is required to draw the liquid into the stream of pressurized gas that causes nebulization of the liquid. An example of such a nebulizer is disclosed in U.S. Pat. No. 4,588,129. The aerosol is then inhaled by the patient. Typically, the aerosol production is continuous, so a vent is typically provided to ensure that the pressure differential created by the jet operates continuously and consistently. The drug reservoir in nebulizers is usually a cone, cup, or bowl-shaped vessel into which a sterile aqueous solution of the drug is added.

Other nebulizer methods besides gas-jet nebulizers are known, for example ultrasonic nebulizers and vibrating mesh nebulizers.

Typical drugs used with nebulizers are drugs for the treatment of asthma and obstructive pulmonary diseases, but other pulmonary and systematic medications may be administered by inhalation with nebulizers. For example, albuterol (called salbutamol in many countries), used for treating asthma and bronchospasm, may be administered as a nebulized solution. Another example is pentamidino, a drug used to treat *Pneumocystis carinii* pneumonia (PCP) (also called *Pneumocystis jirovecii*). Many other medications are useful or potentially useful as inhaled drugs and can potentially be used with a nebulizer.

Nebulizers are particularly useful for the administration of inhaled drugs to small children, elderly, unconscious, or disabled patients who cannot coordinate their breathing or take instruction on the use of coordinated inhalation devices, such as a metered dose inhaler. Also, nebulizers may be used with an inhalation mask for patients who cannot use a mouthpiece to inhale the drug. With a nebulizer, the dose of drug is administered to the patient over a period of several minutes, and possibly ten to twenty (or more) tidal or slow deep inhalations per minute, so breathing coordination is not required.

Nebulizers are typically equipped with a mouthpiece that a patient can insert in their mouth, making an airtight seal with their lips while inhaling through the mouth to ingest the nebulized medication into the lungs. In the case of patients who cannot hold a mouthpiece in their mouth or close their lips round the mouthpiece to create a seal, an inhalation mask may be used with a nebulizer. An example of such a mask is disclosed in PCT International Application WO 2012/173993.

In breath-actuated nebulizers, nebulization of the drug only occurs during inhalation by the patient. Breath-actuated nebulizers have a means for stopping the nebulization or flow of aerosol during exhalation or other intervals when the patient is neither inhaling or exhaling. Such devices are known, for example, from Denyer in U.S. Pat. No. RE40591, and Grychowski et al., in U.S. Pat. Nos. 5,823,179 and 6,644,304. A breath-actuated nebulizer has been marketed in the United States under the brand name AEROECLIPSE® by Monaghan Medical, and by Trudell Medical International in other countries.

Breath-actuated nebulizers may have significant advantages over conventional nebulizers. In conventional nebulizers, the drug is aerosolized continuously regardless of whether the patient is inhaling or not. Conventional nebulizers typically are vented to the atmosphere, so aerosol that is not inhaled is vented to the air in front of the patient. This wastes drug, and exposes others (including caregivers) in the vicinity to the aerosolized drug. In addition, the dosage is impossible to precisely determine because of this drug loss. In many cases, these shortcomings are not a problem, due to the low cost of conventional (continuous) nebulizers, and the low toxicity and low cost of drug of many of the drugs used in conventional nebulizers.

However, in the case of expensive drugs or drugs that may be toxic or sensitizing to others in the vicinity of the patient, conventional nebulizers are much less desirable than a breath-actuated nebulizer. With a breath-actuated nebulizer, the dosage can be precisely metered, and very little of the drug is wasted, since nebulization is stopped when the patient is not inhaling.

BRIEF SUMMARY

In an embodiment, this invention provides a breath triggered gas jet nebulizer comprising a generally cylindrical body in a horizontal orientation to the patient. Within the body is a Venturi configured to nebulize a solution of a drug stored in a reservoir. Within the body is a shaft integrated with a baffle and diaphragm that moves horizontally in response to the breathing of a patient. When the patient is inhaling the diaphragm flexes shifting the baffle toward the patient and over the Venturi, allowing nebulization to occur. When the patient's inhalation stops, the diaphragm flexes to a default position in which the baffle is shifted to a position distal to the Venturi, thereby stopping the nebulization.

DETAILED DESCRIPTION

The nebulization action in the gas jet nebulizers disclosed herein for administering medication to humans or animals by inhalation depends on a device with a reservoir containing a solution with a drug dissolved therein, and a Venturi effect with a high pressure jet orifice and one or more liquid orifices adjacent to the jet, wherein a baffle or deflector impinges on the jet a short distance above the jet orifice. One or more liquid orifices adjacent to the Venturi orifice are in communication with liquid tubes or capillaries fed by a drug reservoir containing a solution of drug. The nebulization or aerosolization (these terms are used interchangeably herein), presumably occurs because the baffle deflects the low pressure zone created by the Venturi over the liquid orifices. Without being bound by any theory of operation, it is believed that the reduced pressure created by the Venturi jet impinging on the baffle draws the drug solution through the liquid orifices, and the jet aerosolizes the liquid as it exits the liquid orifices from shearing effects. The baffle typically also performs a secondary function of deflecting large droplets and forcing them back into the drug reservoir, since in a drug nebulizer, only very small droplets that freely float in air are desired as an inhaled aerosol. Without the baffle, the liquid orifices are presumably not subject to the effect of the Venturi low pressure zone and no liquid is drawn out of the liquid orifices, and no aerosolization occurs. Thus, in this invention, a movable baffle is provided in a horizontal plane, such that when the baffle is directly over the Venturi, nebulization occurs, and when the baffle is moved horizontally away from the Venturi, nebulization stops. In this invention, by moving the baffle into a nebulizing position in response to the inhalation of a patient, the nebulization only occurs when the patient is inhaling, and no nebulization occurs when the patient is exhaling or otherwise not exerting an inhalation. This movement of the baffle that creates or stops nebulization is termed "breath triggered" or "breath actuated" (which terms are used interchangeably) nebulization.

In an embodiment of this invention, a breath triggered nebulizer is provided for the administration of inhaled medication to a patient, said nebulizer having horizontal and vertical axes, comprising a horizontally oriented cylindrical body defining an upper chamber airway; a vertically oriented lower chamber having therein a liquid reservoir containing a medicament in solution, wherein said liquid reservoir defines the horizontal axis; a pressurized gas inlet port in fluid communication with a gas jet; a liquid channel surrounding the gas inlet port, said liquid channel in fluid communication with a liquid orifice, wherein the gas jet is adjacent to the liquid orifice, and the gas jet is oriented vertically; a horizontally movable baffle comprising a first position at a predetermined distance from the gas jet such that a pressure differential is created in the liquid channel that draws liquid through the liquid channel and causes nebulization by the interaction of the gas jet and liquid orifice; wherein the baffle has a second default position distal from the gas jet such position at a distance from the gas jet so that the pressure differential is insufficient to draw liquid into the liquid channel, and no nebulization of the liquid occurs; wherein the baffle movement is controlled by a horizontal channel between the first and second positions at a fixed vertical distance relative to the gas jet; and wherein the baffle is moved from the second position to the first position by the inhalation by the patient, and the baffle shifts to the second position when the patient is not inhaling.

Figure 1A:
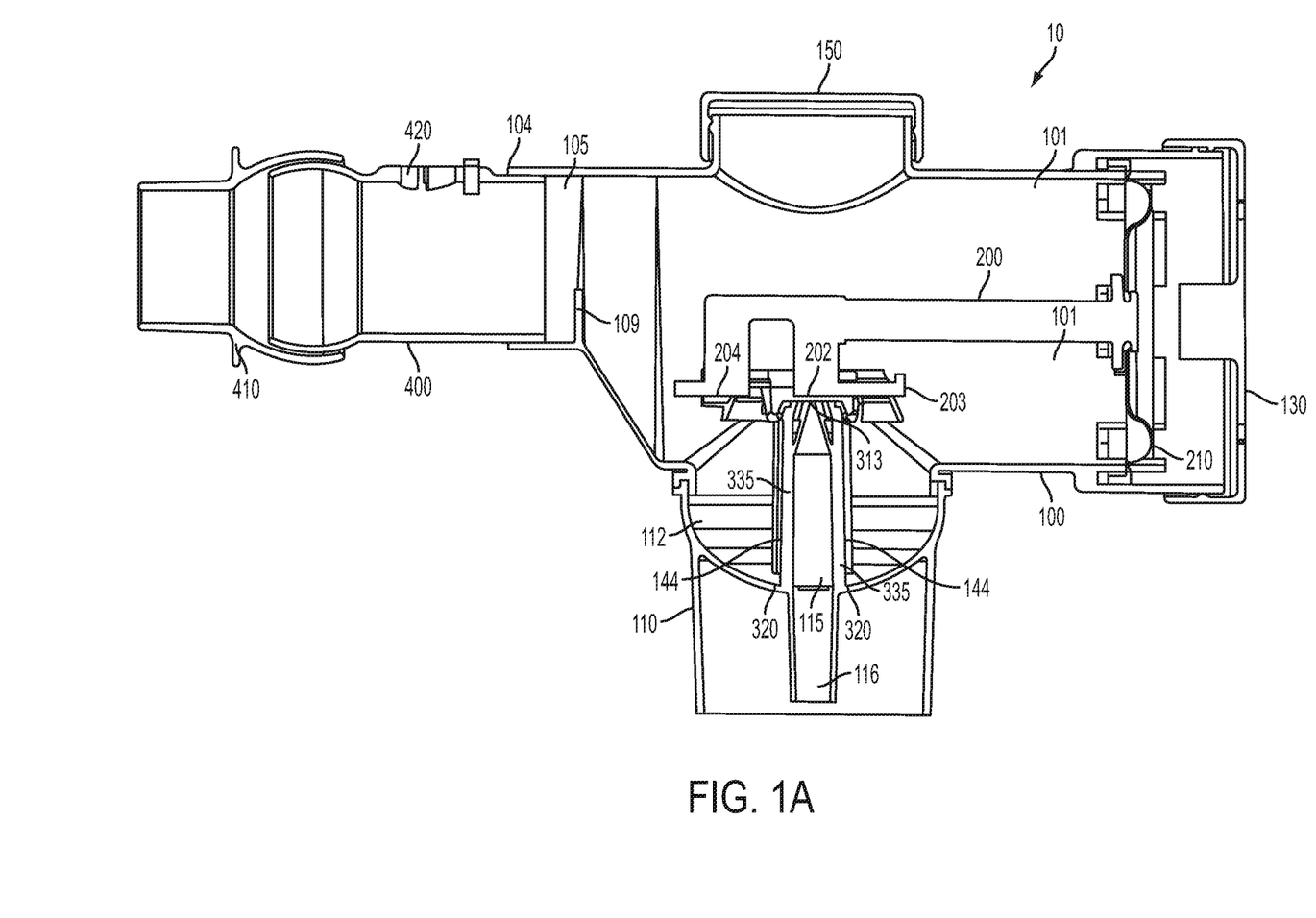
FIG. 1A is a cross-section of the nebulizer in the nebulization mode.
Figure 1B:
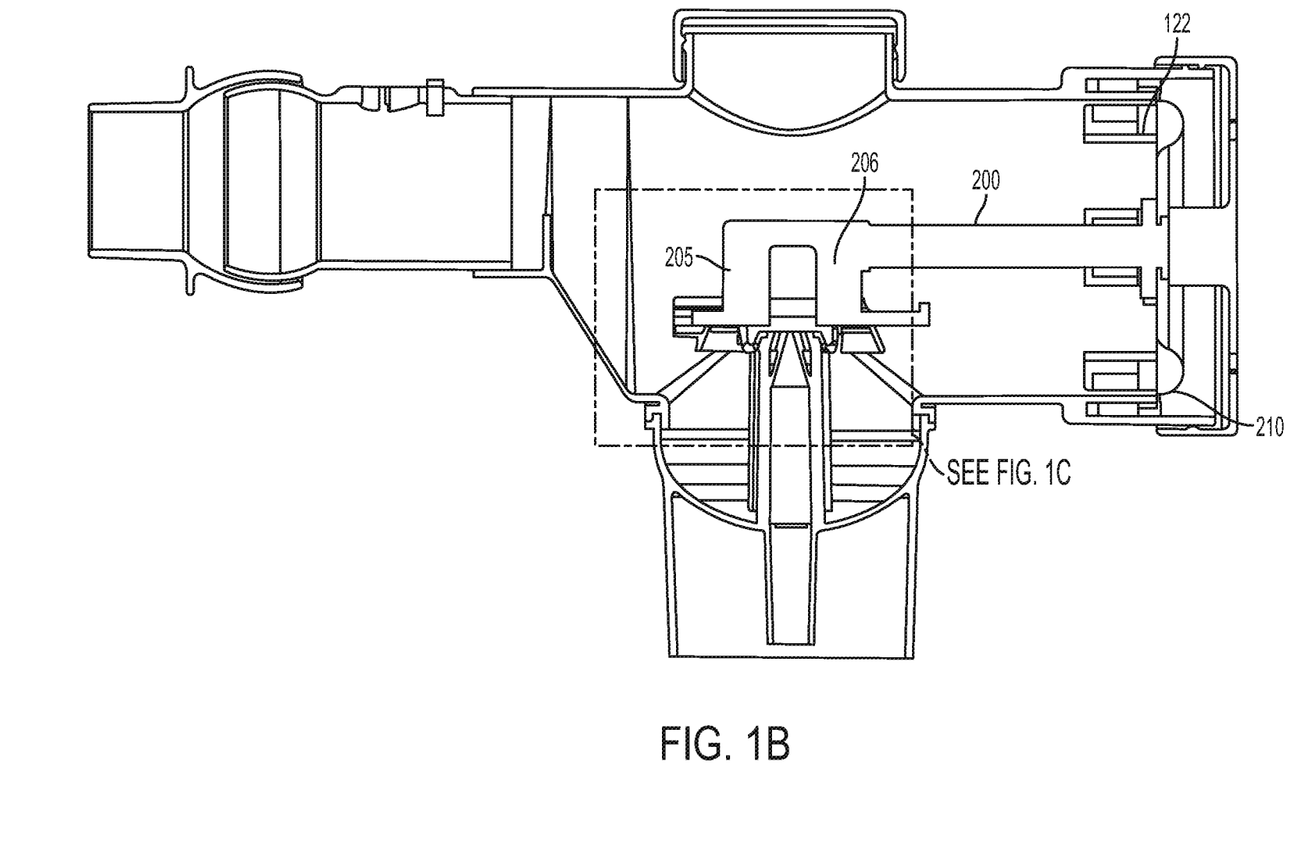
FIG. 1B is a cross-section of the nebulizer in the non-nebulization mode.
Figure 1C:
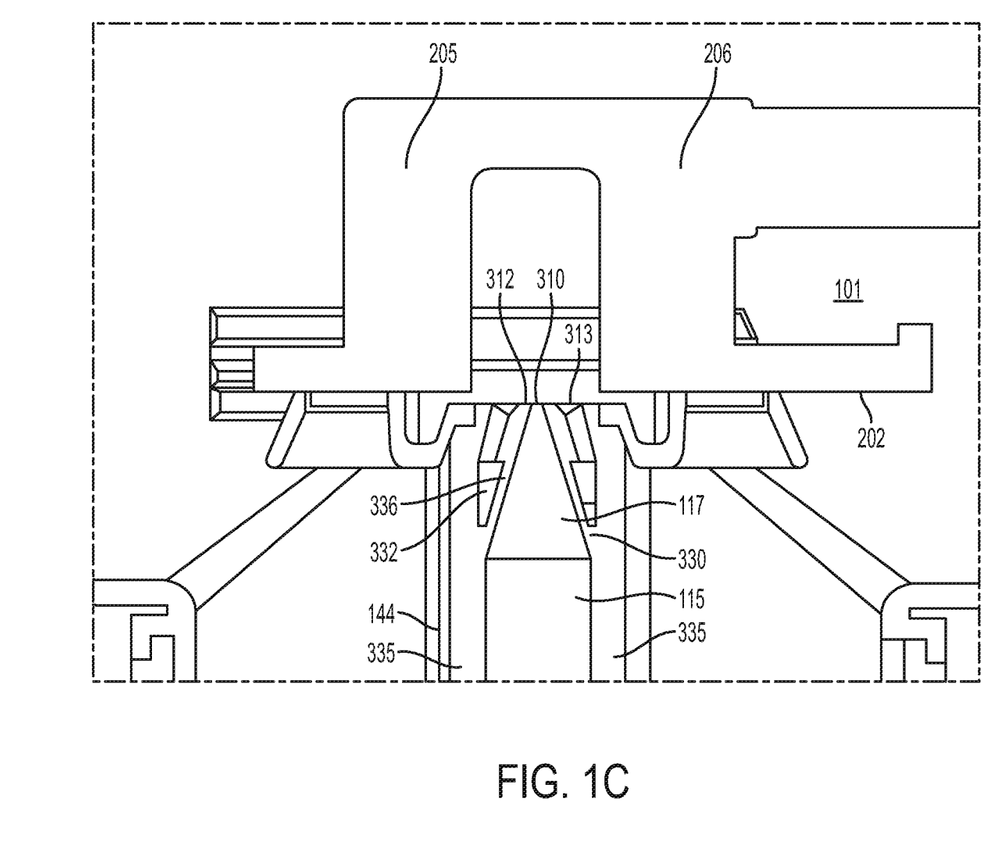
FIG. 1C is a detail cross-section of a portion of FIG. 1B

Thus, the inventive nebulizer 10 in the Figures has defined horizontal and vertical axes. In one aspect, the horizontal axis is defined by the drug reservoir 112, which must generally remain generally level because it contains a liquid. In another aspect, the horizontal axis may be defined by a line through the center of the generally cylindrical body 100, from the airway end 104 to the back of the apparatus at cap 130. Thus, as shown in FIGS. 1A and 1B, the horizontal and vertical axes are as drawn, i.e., the vertical axis is top to bottom, and the horizontal axis is right to left. Thus, cap 150 is at the top of the device, and lower body 110 is at the bottom of the device.

Body 100 of the nebulizer 10 comprises a main section that is cylindrical in shape, is oriented horizontally, and defines an interior chamber 101. The ventral side of body 100 has a circular opening 106 connected to lower body 110. Lower body 110 includes a drug reservoir 112 that in operation would be filled with a liquid medication. Reservoir 112 is a cup shaped vessel that narrows at the bottom and feeds the drug solution into opening 820 for inspiration into the Venturi.

The Venturi is integral with lower body 110. The Venturi comprises a pressurized gas inlet stem 116 and pressurized gas tube 115. At the top of tube 115, at least one liquid window 330 is provided, with section 332 above the window. Tube 115 narrows in the conical section 117, leading to Venturi orifice 310. A passageway 336 is defined between section 332 and section 117. At the top of passageway 336 is one or more liquid orifices 312 through which the drug solution will pass during nebulization. Stem 144 fits over tube 115, defining a narrow passageway 335 for the drug solution to pass during nebulization. The drug solution is fed into passageway 885 through an opening 320 at the bottom of stem 144. During nebulization, the drug solution is drawn through opening 820, up passageway 335, and through windows 330. The drug solution then moves into passageway 336 and exits from orifices 312. The drug solution is then aerosolized in the space of chamber 101 on exposure to the high velocity low pressure local environment in the Venturi during nebulization.

In an embodiment, the Venturi orifice 310 and the orifices 312 are situated on a planar surface 313 and all of orifices 310 and 312 are on the same plane.

The dorsal side of body 100 may contain a circular opening 108 which is covered by top cap 150. Top cap 150 is intended to be easily removable, and can be used to add the drug solution to the reservoir 112 with a pipette or by simply pouring a solution of drug into the reservoir 112.

The anterior end of body 100 (the end closest to the patient) comprises opening 104 which defines the airway 105 by which aerosolized drug is exhausted from the nebulizer during inhalation into the mouth or nose of a patient. The aerosolized drug then travels to the lungs of the patient during inhalation. In an embodiment, baffle 109 is situated in the airway aft of opening 105. If present, baffle 109 blocks about the lower third of opening 105, and helps to ensure that only freely floating aerosol particles are inhaled by the patient. Baffle 109 helps to block the ingestion of larger aerosol particles from being inhaled.

In an embodiment, as illustrated in the drawings, opening 105 is in communication with adapter 400 and swivel adapter 410. A mouthpiece or mask may be connected to airway 430 on swivel adapter 410 in this embodiment. Also shown is exhaust valve 420, in the illustrated embodiment integrated to adapter 400. An embodiment of exhaust valve 420 is shown with flap 422, made from a flexible rubber material that provides a tight seal during inhalation but flexes open to exhaust exhaled air during exhalation. Other configurations of the exhaust valve are possible. An exhaust valve is necessary in this nebulizer because there is no other vent or pressure equalization provided in body 100 for exhaled air.

The posterior end of body 100 comprises a circular opening 102 that is connected end cap 130. A series of vents 132 are in cap 130. A series of one-way vents 132 are in cap 130 that permit air to enter to equalize pressure during inhalation, but are sealed during exhalation.

Figure 2A:
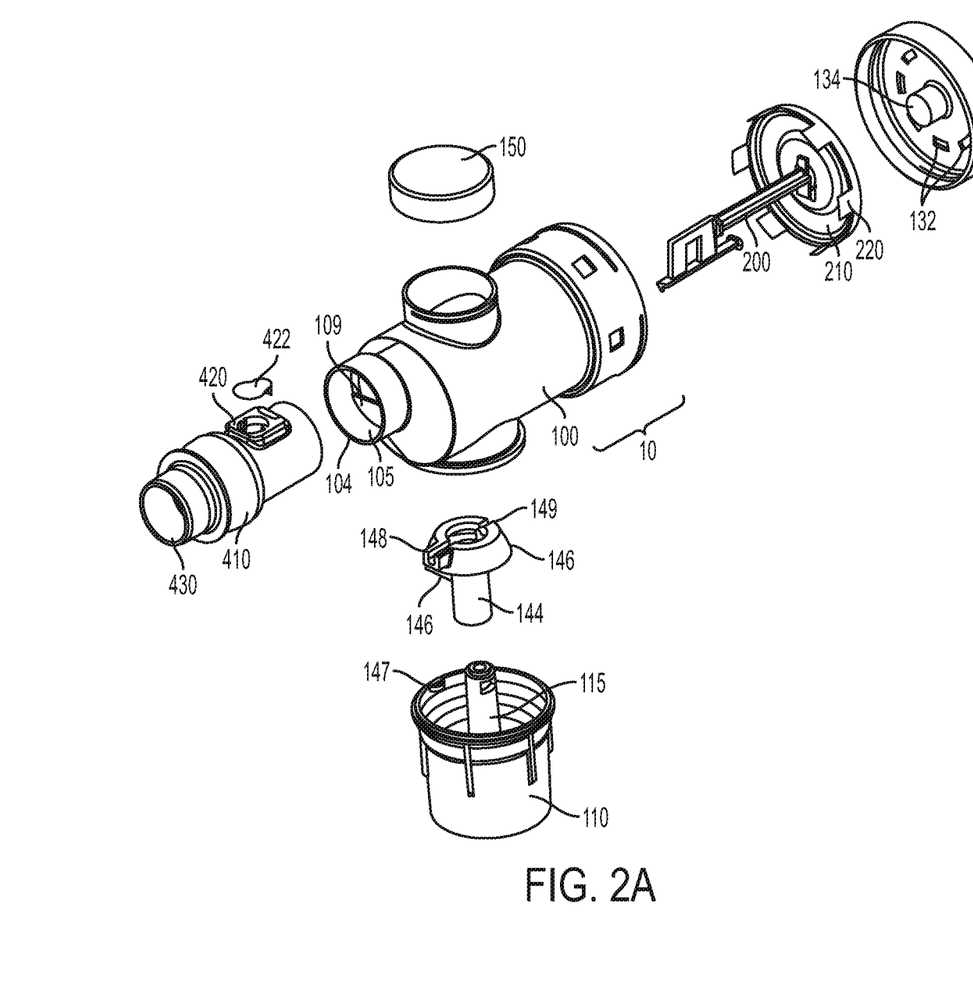
FIG. 2A is an exploded view from an anterior viewpoint.
Figure 2B:
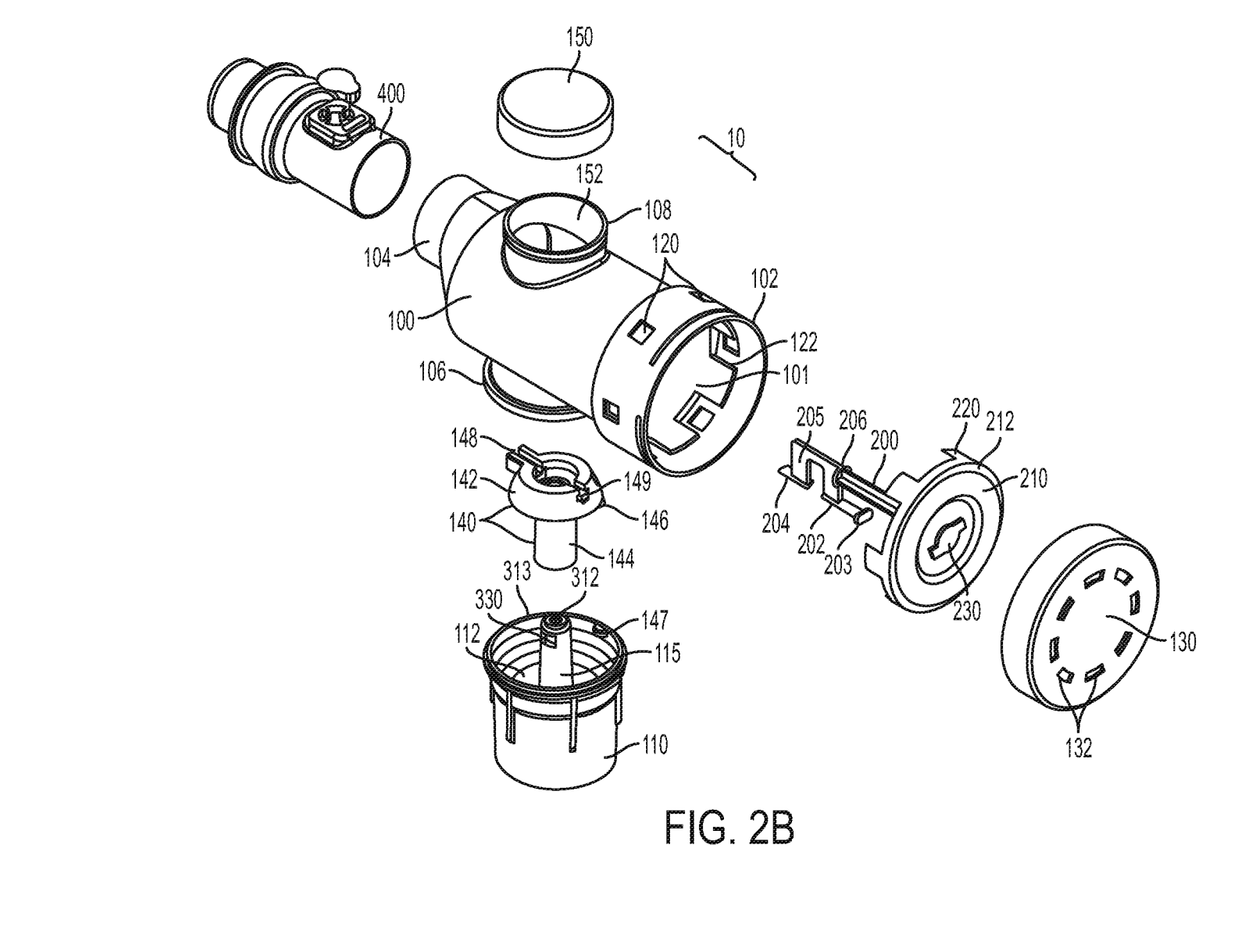
FIG. 2B is an exploded view from a posterior viewpoint.
Figure 3A:
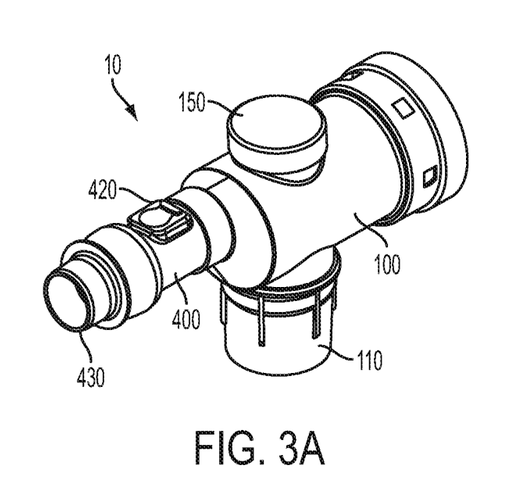
FIG. 3A is a perspective view of the assembled nebulizer from an anterior viewpoint.
Figure 3B:
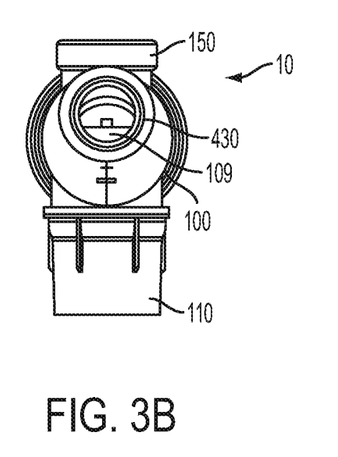
FIG. 3B is an elevation view of the front (anterior) end of the nebulizer.
Figure 3C:
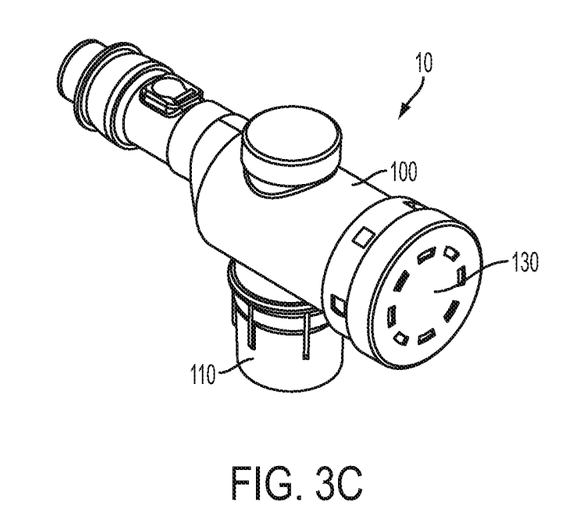
FIG. 3C is a perspective view of the assembled nebulizer from an posterior viewpoint.
Figure 4A:
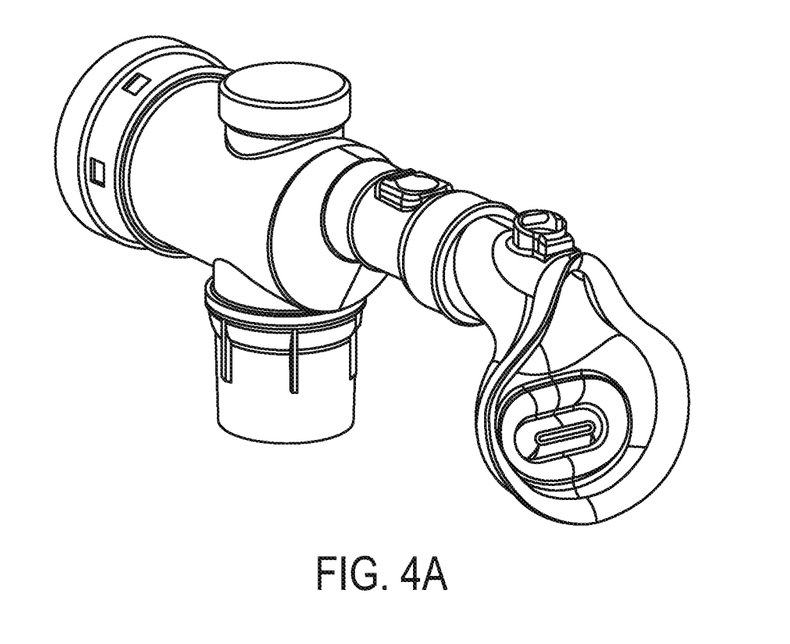
FIG. 4A is a perspective view of the inventive nebulizer with an inhalation mask connected to the airway of the nebulizer.
Figure 4B:
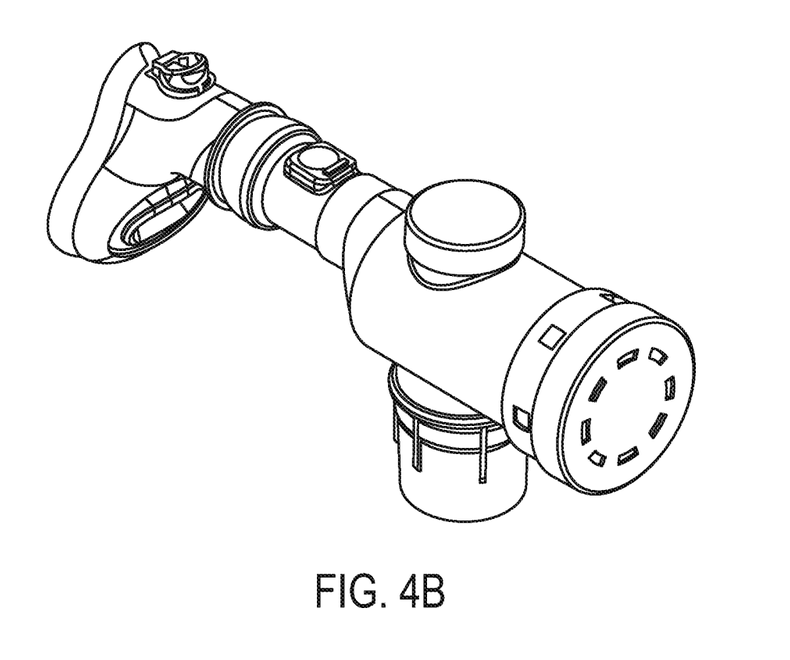
FIG. 4B is a different perspective view of the inventive nebulizor with an inhalation mask connected to the airway of the nebulizer.
Figure 5A:
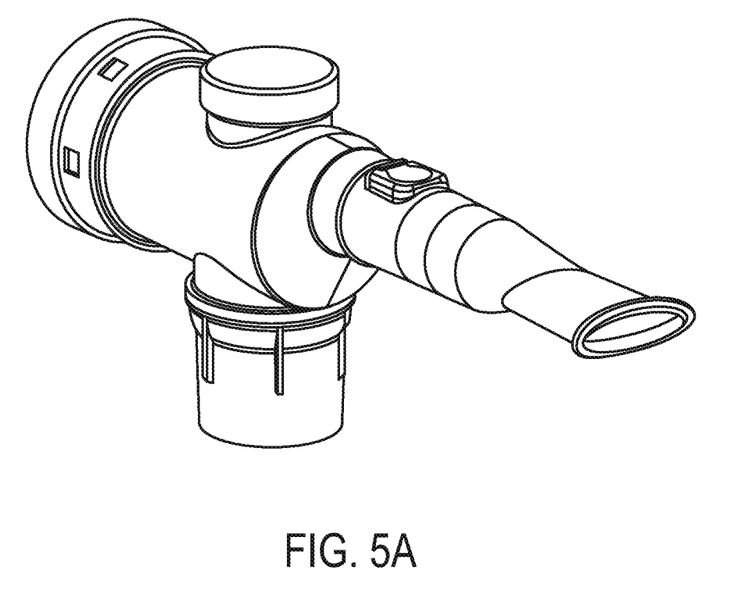
FIG. 5A is a perspective view of the inventive nebulizer with a mouthpiece connected to the airway of the nebulizer.
Figure 5B:
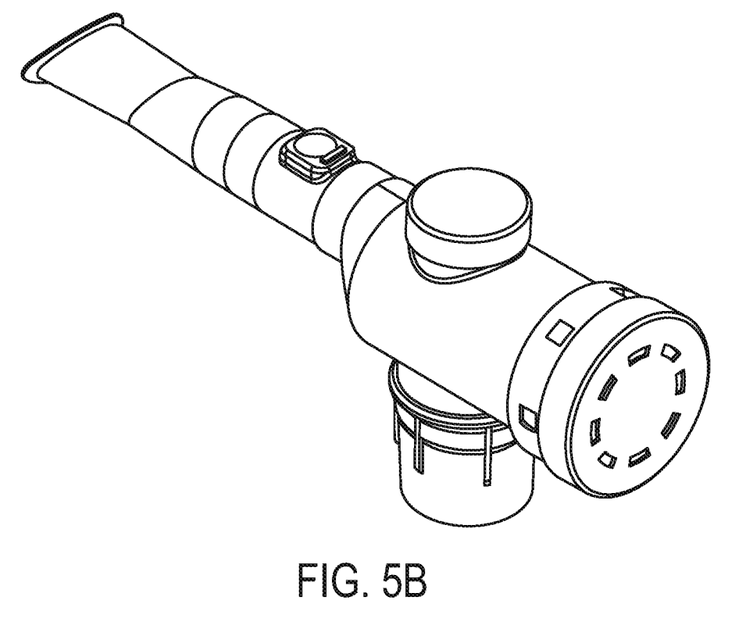
FIG. 5B is a different perspective view of the inventive nebulizer with a mouthpiece connected to the airway of the nebulizer.

Channel support 140 is an integrated part that includes vertical shaft 144 and cap portion 142. Shaft 144 defines a pipe that nests over gas tube 115. The space between shaft 144 and tube 116 is liquid passage 335. Cap portion 142 contains baffle guide channels 148 and 149. Alignment tab 146 protrudes from vertical shaft 144 on the left side as illustrated in FIG. 2A, and serves to align support 140 with respect to the movable baffle. Tab 146 fits into slot 147 on lower body 110.

Within body 100 is integrated shaft assembly 200, which includes diaphragm 210 and the Venturi baffle 202. Diaphragm 210 is supported peripherally by ring 212, which is torsionally inflexible, and nests in indents 122, part of body 100. The diaphragm 210 is made from a flexible material such as a soft rubber, and can easily flex in response to the patients breathing. The center of diaphragm 210 is connected to shaft 200. The anterior end of shaft 200 contains supports 205 and 206. Guide skid 204 is connected to 205, and baffle 202 is connected to 206. The posterior end of baffle 202 contains tab 203, that acts as a backstop, preventing further forward motion of shaft 200 during inhalation, when the shaft moves forward.

This nebulizer is termed "breath triggered" because the action of inhalation during use starts nebulization of a drug, and nebulization of the drug ceases when inhalation ceases, either during exhalation or any other point when the patient is not inhaling, that it, drawing air into the patients' lungs naturally. During inhalation, the breathing action creates a negative pressure in the chamber 101 of the nebulizer 10. This flexes the diaphragm 210 forward, which moves baffle 202 from the default non-nebulization position to the nebulization position, by shifting the integral shaft 200 and movable baffle 202 to a position directly over the Venturi jet, thereby causing aerosolization to occur when the liquid orifices 312 are subject to the high velocity low pressure local environment from the Venturi. This movement is illustrated by cross-section views in FIGS. 1B and 1A. FIG. 1B is the default, non-inhalation position. The diaphragm is biased to the position as shown in FIG. 1B when no inhalation is occurring. During inhalation, the negative pressure in chamber 101 draws diaphragm 210 forward, as shown in FIG. 1A, and moves shaft 200 and baffle 202 to cause nebulization to occur. The diaphragm must be designed to be sufficiently sensitive to low inhalation flow velocities, for example from highly diseased persons with very weak inspiratory ability, or small children, yet still provide sufficient force to move the shaft to the nebulization position. In an embodiment, the diaphragm may be designed to move within a range of inhalation flow rates of 0.5 L/min in new born infants to 15 L/min in adults.

When inhalation ceases, the diaphragm flexes in a posterior direction to its default position, returning to the configuration shown in FIG. 1B, drawing movable baffle 202 rearward so that the Venturi jet is vented into the space between supports 205 and 206. Without the baffle directly over the Venturi, no nebulization occurs, because the jet vents directly upward, and the liquid orifices 312 are not subject to the Venturi effect, so no liquid is drawn through the orifices 312.

The vent ports 120 equalize pressure during inhalation, preventing a vacuum from developing in the main body of the nebulizer. Flexible flaps 220, which are integral with the diaphragm 210 rest in indents in section 122, and cover ports 120 from the interior chamber 101. During exhalation or when breathing is relaxed, the flaps prevent air and aerosolized drug in the interior chamber 101 from escaping from the nebulizer. During inhalation, the negative pressure in the interior chamber 101 opens the flaps to equalize the air pressure in the chamber 101.

In an embodiment, a noise making feature may be provided that makes a clicking sound during inhalation. As shown in the figures, this may comprise protrusion 230 that rests in cavity 134 on the interior of end cap 132. During inhalation, when the shaft assembly 200 is drawn forward, the action of protrusion 280 moving in cavity 184 may make a clicking sound. In an embodiment, when the shaft assembly 200 moves back to its default position during exhalation, 230 and 134 hit each other making a clicking sound.

The interface with the inventive apparatus and the patient is a mouthpiece or inhalation mask. A mouthpiece may comprise various embodiments. In an embodiment, a mouthpiece may be a generally cylindrical or ovoid (in cross section) appendage suitable for insertion into the mouth of the patient. The patient then wraps his or her lips around the mouthpiece to make a seal and proceeds to inhale and exhale to receive the nebulized drug. In another embodiment, a mouthpiece may have a flattened portion for insertion into the mouth and lips.

In another embodiment, an inhalation mask may be employed that covers the mouth and/or nose of the patient. The mask would have a suitable inlet for connecting to airway 105 to receive the nebulized medication that is transmitted to the mouth and/or nose of the patient. Small children, in particular, are obligate nasal breathers. In the case of an inhalation mask, an exhaust valve is mandatory, because there is no pressure equalization outlet in the inventive nebulizer apparatus to vent exhaled air. Such an exhaust valve may be integrated into the mask, or it may be on a linking part between the nebulizer and the mask, shown for example as part 420 in the drawings. With any exhaust valve embodiment, a further optional embodiment is a filter to trap and prevent substantially all of the active drug from entering the outside air in front of the patient. In some case, active drug can harm nearby persons including caregivers, and may even harm the patient, for example by causing eye irritation. The use of a filter can prevent this problem.

Various embodiments of the inventive nebulizer and a mouthpiece or inhalation mask are shown in FIGS. 4 and 6. FIGS. 4A and 4B show an inhalation mask connected to the inventive nebulizer with a swivel adapter. A variety of masks may be employed with the inventive nebulizer. The mask shown in FIGS. 4A and 4B is described in international patent application PCT/US2012/042055, and has a soother device orifice, through with a nipple may be inserted for use with a small child who would suck on the nipple while inhaling medication through the mask with an airway aligned with nose of the patient. In another embodiment (not shown), the mask may not have a soother device orifice.

FIGS. 5A and 5B illustrate the nebulizer with a mouthpiece that a competent older child or adult would typically use. The mouthpiece is inserted into the mouth of the patient and the patient forms a seal around the mouthpiece with their lips while inhaling a drug using the nebulizer. By the term "competent" it is meant here that the patient is conscious and can accept and understand instructions.

By the term "medicament" as used herein is meant a drug suitable for administration directly into the lungs of a patient.

This invention provides both a nebulizer apparatus 10 and a method of administering a drug to a patient with a nebulizer 10. In the method of administering a drug to a patient, a solution of a drug is added to reservoir 112 through opening 152, a source of pressurized medical gas, such as air or medical oxygen is connected to stem 116. In various embodiments, a mouthpiece fitted to the inventive nebulizer is inserted into the patients mouth, or a mask is connected to the nebulizer that is held by a caregiver over the mouth and nose of a patient. When the patient inhales, the nebulizer 10 will provide atomized drug that will enter the lungs of the patient. When the patient is not inhaling, such as during an exhalation or during periods when the patient is neither inhaling nor exhaling, the atomization stops. Accordingly, there is minimal wasted drug as compared to conventional nebulizers that nebulize drug continually regardless of whether a patient is inhaling or not, and the dose of the drug can be more accurately determined, since there is minimal wastage.

What is claimed is:

1. A breath triggered nebulizer for the administration of inhaled medication to a patient, said nebulizer having an upper chamber airway and horizontal and vertical axes, comprising:

a) a horizontally oriented cylindrical body defining the upper chamber airway, said horizontally oriented cylindrical body having a distal end and a proximal end;

b) a vertically oriented lower chamber having therein a liquid reservoir for containing a medicament in solution, wherein said liquid reservoir defines the horizontal axis;

c) a pressurized gas inlet port configured to be in fluid communication with a gas jet;

d) a liquid channel surrounding or adjacent the gas inlet port, said liquid channel in fluid communication with a liquid orifice, wherein the gas jet is adjacent to the liquid orifice, and the gas jet is oriented vertically;

e) a horizontally movable shaft assembly within the upper chamber airway, the shaft assembly comprising a flexible diaphragm and a baffle at an end of the shaft assembly opposite the flexible diaphragm, said flexible diaphragm being located at said distal end of the horizontally oriented cylindrical body, the shaft assembly further comprising (i) a first position wherein the baffle is at a predetermined distance from the gas jet such that a pressure differential is created in the liquid channel that draws the medicament solution through the liquid channel and causes nebulization of the medicament solution by the interaction of the gas jet and liquid orifice, and (ii) a second position wherein the baffle is at a distance distal from the gas jet such that the pressure differential is insufficient to draw liquid into the channel and no nebulization occurs;

whereby movement of the baffle is controlled by a tab extending from the shaft assembly between the first position and the second position at a fixed vertical distance relative to the gas jet;

whereby the shaft assembly is moved from the second position to the first position during inhalation by the patient which flexes the diaphragm in a forward direction, and whereby the shaft assembly shifts to the second position when the patient is not inhaling, which flexes the diaphragm in a posterior direction to a posterior position; and whereby the nebulized medicament solution is inhaled by the patient to deliver nebulized medicament solution to lungs of the patient, said nebulizer further comprising a one-way vent that opens during inhalation to permit external air entry into the upper chamber and further comprising an inhalation mask or mouthpiece in fluid communication with the upper chamber airway.

2. The nebulizer of claim 1 wherein an audio signal is produced when the shaft assembly moves from the first position to the second position.

3. The nebulizer of claim 2 wherein the shaft assembly further comprises a protrusion at the distal end of the shaft assembly comprising the flexible diaphragm, the nebulizer further comprising an end cap adjacent the flexible diaphragm, wherein the audio signal is a clicking sound produced by the protrusion contacting a part of the end cap.

4. The nebulizer of claim 1 wherein said gas jet and liquid orifice are on a same horizontal plane.

5. The nebulizer of claim 1 wherein the liquid orifice comprises one or more holes on top of the liquid channel.

6. The nebulizer of claim 1 wherein the liquid orifice comprises a concentric tubular opening in a concentric relationship to the gas jet.

7. The nebulizer of claim 1 wherein the baffle is responsive to inspiratory flow velocity in a range of 0.5 L/min to 15 L/min.

8. The nebulizer of claim 1 wherein an exhalation valve is present on the upper chamber airway.

9. The nebulizer of claim 8 wherein the exhalation valve has a filter that traps substantially all exhaled medication from being expelled from the nebulizer.

10. A method of administering an inhaled medicament to a patient with a nebulizer comprising:
 a) providing the nebulizer of claim 1;
 b) inhaling air from the horizontally oriented cylindrical body to flex the diaphragm and move the shaft assembly from the second position to the first position;
 c) creating a pressure differential in the liquid channel to draw the medicament solution through the liquid channel causing the nebulization of the medicament solution; and
 d) transmitting the nebulized medicament solution to the lungs of the inhaling patient.

\* \* \* \* \*